United States Patent [19]

Drabek

[11] Patent Number: 4,472,429
[45] Date of Patent: Sep. 18, 1984

[54] N-(3-TRIMETHYLSTANNYLPROPYL)CARBAMATES AND USE THEREOF IN PEST CONTROL

[75] Inventor: Jozef Drabek, Oberwil, Switzerland

[73] Assignee: Ciba-Geigy Corporation, Ardsley, N.Y.

[21] Appl. No.: 437,584

[22] Filed: Oct. 29, 1982

[30] Foreign Application Priority Data

Oct. 14, 1982 [CH] Switzerland .......................... 6001/82

[51] Int. Cl.³ .......................... A01N 55/04; C07F 7/22
[52] U.S. Cl. ..................................... 424/285; 424/288; 549/209; 549/212; 260/429.7
[58] Field of Search .............................. 549/209, 212; 260/429.7; 424/285, 288

[56] References Cited

U.S. PATENT DOCUMENTS 4,160,846 7/1979 Strunk et al. ........................ 549/209
4,178,382 12/1979 Mao et al. ........................ 260/429.7

*Primary Examiner*—Henry R. Jiles
*Assistant Examiner*—Bernard Dentz
*Attorney, Agent, or Firm*—Frederick H. Rabin

[57] ABSTRACT

There are disclosed novel N-(3-trimethylstannylpropyl)carbamates, a process for their preparation and their use in pest control. These carbamates have the formula $$(CH_3)_3SnCH_2CH_2CH_2NHCOOR_1$$

wherein $R_1$ is unsubstituted or substituted alkyl, alkenyl, alkynyl, benzyl, phenyl, naphthyl or dihydrobenzofuranyl.

10 Claims, No Drawings

N-(3-TRIMETHYLSTANNYLPROPYL)CARBAMATES AND USE THEREOF IN PEST CONTROL

The present invention relates to N-(3-trimethylstannylpropyl)carbamates, to a process for the preparation thereof and to a method of use thereof in pest control.

The N-(3-trimethylstannylpropyl)carbamates have the formula

  (I)

wherein $R_1$ is unsubstituted or substituted alkyl, alkenyl, alkynyl, benzyl, phenyl, naphthyl or dihydrobenzofuranyl.

The possible alkyl, alkenyl and alkynyl groups may be straight chain or branched and contain preferably 1 to 6 and 2 to 6 carbon atoms respectively in the chain. Examples of such groups comprise: methyl, ethyl, propyl, isopropyl, n-butyl, n-pentyl, n-hexyl and the isomers thereof, allyl, methallyl, ethynyl and propynyl. Preferred substituents of these groups are hydroxy, cyano, fluorine, chlorine, bromine, iodine, $C_1$–$C_6$alkoxy, $C_1$–$C_6$alkylthio, dimethylamino or phenyl.

Preferred substituents at the benzyl, phenyl, naphthyl or dihydrobenzofuranyl group are: fluorine, chlorine, bromine, iodine, $C_1$–$C_6$alkyl, $C_1$–$C_6$alkoxy, nitro, cyano or $C_1$–$C_6$haloalkyl and, in particular, trifluoromethyl.

Preferred compounds of the formula I are those wherein $R_1$ is $C_1$–$C_6$alkyl which is unsubstituted or substituted by hydroxy, cyano, fluorine, chlorine, bromine, iodine or $C_1$–$C_6$alkoxy, or is 2,2-dimethyl-2,3-dihydrobenzofuranyl or unsubstituted $C_2$–$C_6$alkenyl, $C_2$–$C_6$alkynyl, benzyl, phenyl or naphthyl.

Particularly preferred compounds of the formula I are those wherein $R_1$ is $C_1$–$C_6$alkyl which is unsubstituted or substituted by $C_1$–$C_6$alkoxy, or is $C_2$–$C_6$alkenyl, 2,2-dimethyl-2,3-dihydrobenzofuranyl, phenyl or benzyl.

The compounds of formula I may be prepared by methods which are known per se, e.g. in accordance with the following reaction scheme:

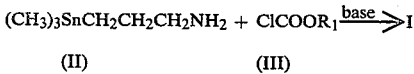

$R_1$ in formula III is as defined for formula I.

Suitable bases are in particular tertiary amines such as trialkylamines, dialkylanilines and p-dialkylaminopyridines.

The process is carried out under normal pressure in the temperature range from $-25°$ to $150°$ C., preferably from $50°$ to $100°$ C., and optionally in a solvent or diluent.

Examples of suitable solvents or diluents are: ethers and ethereal compounds such as diethyl ether, diisopropyl ether, dioxan and tetrahydrofuran; aromatic hydrocarbons such as benzene, toluene and xylenes; ketones such as acetone, methyl ethyl ketone and cyclohexanone; nitriles such as acetonitrile; esters such as ethyl acetate and butyl acetate; and dimethylformamide, dimethylsulfoxide, methyl cyanide and halogenated hydrocarbons.

The starting materials of the formulae II and III are known and may be prepared by known methods.

The compounds of formula I are suitable for controlling pests of animals and plants. In addition, these compounds also have fungicidal and plant regulating properties.

In particular, the compounds of formula I are suitable for controlling insects e.g. of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and mites and ticks of the order Acarina.

In particular, the compounds of the formula I are suitable for controlling plant-destructive insects, especially plant-destructive feeding insects, in ornamentals and crops of useful plants, especially in cotton, vegetables, rice and in fruit.

The compounds of the formula I are also very effective against eating and biting insects and against flies, for example Musca domestica and mosquito larvae.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. Just as with the nature of the compositions, the methods of application, such as spraying atomising, dusting, scattering or pouring, are chosen in accordance with the intended objectives and the prevailing circumstances. The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the active ingredient of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives of alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, and phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxyethanols, castor oil polyglycol ethers, polypropylene/polyethylene oxide adducts, tributylphenoxypoly-ethoxyethanol, polyethylene glycol and octylphenoxypoly-ethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1979.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers, in order to produce special effects.

FORMULATION EXAMPLES

Formulation Examples for liquid active ingredients of the formula I (throughout, percentages are by weight)

| (1) Emulsifiable concentrates | (a) | (b) | (c) |
|---|---|---|---|
| active ingredient | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexane | — | 15% | 20% |
| xylene mixture | 65% | 25% | 20% |

Emulsions of any required concentration can be produced from such concentrates by dilution with water.

| (2) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| ligroin (boiling range 160–190° C.) | — | — | 94% | — |

These solutions are suitable for application in the form of microdrops.

| (3) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (4) Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| (5) Wettable powders | (a) | (b) | (c) |
|---|---|---|---|
| active ingredient | 25% | 50% | 75% |
| sodium lignosulfonate | 5% | 5% | — |
| sodium laurylsulfate | 3% | — | 5% |

| (5) Wettable powders | (a) | (b) | (c) |
|---|---|---|---|
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is throughly ground in a suitable mill, affording wettable powders which can be diluted with water to give suspensions of the desired concentration.

| (6) Emulsifiable concentrate | |
|---|---|
| active ingredient | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50%. |

Emulsions of any required concentration can be obtained from this concentrate by dilution with water.

| (7) Dusts | (a) | (b) |
|---|---|---|
| active ingredient | 5% | 8% |
| talcum | 95% | — |
| kaolin | — | 92% |

Ready-for-use dusts are obtained by mixing the active ingredient with the carriers, and grinding the mixture in a suitable mill.

| (8) Extruder granulate | |
|---|---|
| active ingredient | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

| (9) Coated granulate | |
|---|---|
| active ingredient | 3% |
| polyethylene glycol 200 | 3% |
| kaolin | 94%. |

The finely ground active ingredient is uniformly applied, in a mixer, to the kaolin moistened with polyethylene glycol. Non-dusty coated granulates are obtained in this manner.

| (10) Suspension concentrate | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

EXAMPLE 1

Preparation of N-(3-trimethylstannylpropyl)ethyl carbamate

A solution of 2.44 g of ethyl chloroformate in 10 ml of toluene is added dropwise at 5° C. to a solution of 4.99 g of 3-trimethylstannylpropylamine and 4.83 ml of triethylamine in 50 ml of toluene over 15 minutes. The reaction mixture is stirred for 10 hours at 20° C. and washed with three 100 ml portions of water. The organic phase is dried over sodium sulfate and the solvent is distilled off, to give compound 1 of the formula $(CH_3)_3SnCH_2CH_2CH_2NHCOOC_2H_5$ with a refractive index of $n_D^{20°} = 1.4840$.

The following compounds are also prepared in corresponding manner:

2. 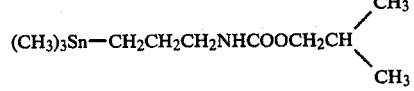   $n_D^{20°} = 1.4789$

3. 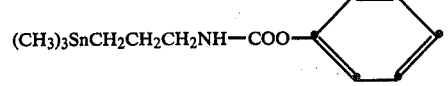   $n_D^{20°} = 1.5329$

4. $(CH_3)_3SnCH_2CH_2CH_2NHCOOCH_2CH_2OCH_3$   b.p.: 107–109° C./0 025 bar 5. (CH₃)₃SnCH₂CH₂CH₂NHCOO— 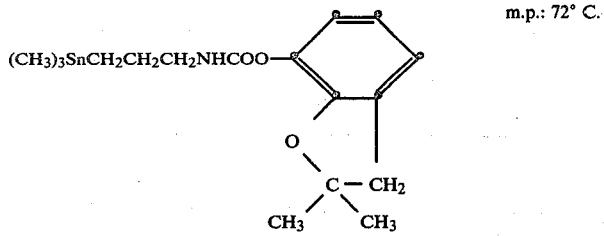  m.p.: 72° C.

6. (CH₃)₃SnCH₂CH₂CH₂NHCOO—CH₂—CH=CH₂    $n_D^{20°}$: 1.4918

7. (CH₃)₃SnCH₂CH₂CH₂NHCOO—CH₂—     $n_D^{20°}$: 1.5309

8. (CH₃)₃SnCH₂CH₂CH₂NHCOO—C₄H₉₍ₙ₎    $n_D^{20°}$: 1.4793

EXAMPLE 2

Insecticidal contact action against Aphis craccivora

Before the start of the test, bean plants (Vicia faba) reared in pots are each populated with about 200 insects of the species Aphis craccivora. The treated plants are sprayed 24 hours later dripping wet with a solution containing 200 or 100 ppm of the compound to be tested. Two plants are used for each test compound at its given concentration and a mortality count is made after a further 24 hours.

The compounds of Example 1 act in this test against insects of the species Aphis craccivora as shown in the table.

EXAMPLE 3

Systemic insecticidal action against Aphis craccivora

Bean plants which have grown roots are transplanted into pots containing 600 ccm of soil and then 50 ml of a solution (prepared from a 25% wettable powder) containing 50 ppm or 10 ppm of the compound to be tested are poured direct onto the soil.

After 24 hours the parts of the plants above the soil are populated with lice of the species Aphis craccivora and a plastic cylinder is then slipped over the plants to protect the lice from any possible contact with the test substance either direct or via the gas phase. A mortality count is made 48 and 72 hours respectively after the start of the test. Two plants, each in a separate pot, are used for each test substance at its given concentration. The test is carried out at 25° C. and 70% relative humidity.

The compounds of Example 1 act in this test against insects of the species Aphis craccivora as shown in the table.

BIOLOGICAL TEST RESULTS

The results of the tests carried out in the foregoing Examples are reported in the table, using the following rating to indicate the percentage kill of the pests:
A: 70–100% kill at a concentration of 10 ppm
B: 70–100% kill at a concentration of 50 ppm
C: 70–100% kill at a concentration of 100 ppm
D: 70–100% kill at a concentration of 200 ppm.

| Compounds | Contact action against Alphis craccivora | Systemic action against Alphis craccivora |
|---|---|---|
| 1 | C | A |
| 2 | D | B |
| 3 | C | B |
| 4 | C | A |
| 5 | C | B |
| 6 | C | B |
| 7 | D | B |
| 8 | C | A |

What is claimed is:

1. An N-(3-trimethylstannylpropyl)carbamate of the formula (CH₃)₃SnCH₂CH₂CH₂NHCOOR₁ wherein R₁ is C₁–C₆-alkyl, C₂–C₆-alkenyl or C₂–C₆-alkynyl which are unsubstituted or substituted by hydroxy, cyano, fluorine, chlorine, bromine, iodine, C₁–C₆-alkoxy, C₁–C₆-alkylthio, dimethylamino or phenyl or is benzyl, phenyl, naphthyl or dihydrobenzofuranyl which are unsubstituted or substituted by fluorine, chlorine, bromine, iodine, C₁–C₆-alkyl, C₁–C₆-alkoxy, nitro, cyano or C₁–C₆-haloalkyl.

2. A compound according to claim 1, wherein R₁ is C₁–C₆-alkyl which is unsubstituted or substituted by hydroxy, cyano, fluorine, chlorine, bromine, iodine or C₁–C₆-alkoxy, or is 2,2-dimethyl-2,3-dihydrobenzofuranyl or unsubstituted C₂–C₆alkenyl, C₂–C₆alkynyl, benzyl, phenyl or naphthyl.

3. A compound according to claim 2, wherein R₁ is C₁–C₆-alkyl which is unsubstituted or substituted by C₁–C₆-alkoxy, or is C₂–C₆alkenyl, 2,2-dimethyl-2,3-dihydrobenzofuranyl, phenyl or benzyl.

4. A compound according to claim 3 of the formula (CH₃)₃SnCH₂CH₂CH₂NHCOOC₂H₅.

5. A compound according to claim 3 of the formula (CH₃)₃SnCH₂CH₂CH₂NHCOO— 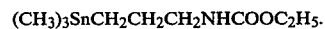 .

6. A compound according to claim 3 of the formula

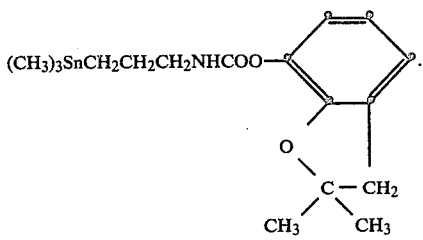

7. A compound according to claim 3 of the formula

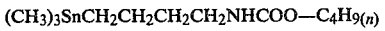

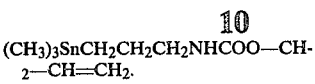

8. A compound according to claim 3 of the formula $(CH_3)_3SnCH_2CH_2CH_2CH_2NHCOO-C_4H_{9(n)}$ 9. A method of controlling insects and acarids, which comprises applying thereto or to the locus thereof a pesticidally effective amount of a compound according to claim 1.

10. An insecticidal and acaricidal composition which comprises (1) from 0.1 to 99% of a compound according to claim 1 as active ingredient, and (2) from 1 to 99.9% of a suitable carrier or other adjuvants.

* * * * *